(12) United States Patent
Owa et al.

(10) Patent No.: US 7,008,414 B2
(45) Date of Patent: **\*Mar. 7, 2006**

(54) LASER TREATMENT APPARATUS

(75) Inventors: Soichi Owa, Kumagaya (JP); Tomoko Ohthuki, Allentown, PA (US)

(73) Assignee: Nikon Corporation, Tokyo (JP)

( * ) Notice: Subject to any disclaimer, the term of this patent is extended or adjusted under 35 U.S.C. 154(b) by 298 days.

This patent is subject to a terminal disclaimer.

(21) Appl. No.: 10/260,287

(22) Filed: Oct. 1, 2002

(65) Prior Publication Data

US 2003/0065312 A1 Apr. 3, 2003

Related U.S. Application Data

(63) Continuation of application No. PCT/JP01/03037, filed on Apr. 9, 2001, and a continuation-in-part of application No. 09/538,233, filed on Mar. 30, 2000, now Pat. No. 6,590,698, which is a continuation of application No. PCT/JP98/05367, filed on Nov. 30, 1998.

(30) Foreign Application Priority Data

Apr. 13, 2000 (JP) .............................. 2000-112248
Mar. 19, 2001 (JP) .............................. 2001-078636

(51) Int. Cl.
*A61B 18/20* (2006.01)
(52) U.S. Cl. .............................. 606/3; 606/4; 359/326
(58) Field of Classification Search ........ 359/326–333; 606/4–5
See application file for complete search history.

(56) References Cited

U.S. PATENT DOCUMENTS

| | | | | |
|---|---|---|---|---|
| 5,324,281 A | * | 6/1994 | Muller | 606/5 |
| 5,423,801 A | | 6/1995 | Marshall et al. | 606/5 |
| 5,624,436 A | | 4/1997 | Nakamura et al. | 606/12 |
| 6,066,127 A | | 5/2000 | Abe | 606/2 |
| 6,099,522 A | * | 8/2000 | Knopp et al. | 606/5 |
| 6,129,722 A | * | 10/2000 | Ruiz | 606/5 |
| 6,149,643 A | * | 11/2000 | Herekar et al. | 606/5 |
| 6,156,030 A | * | 12/2000 | Neev | 606/10 |
| 6,159,202 A | | 12/2000 | Sumiya et al. | 606/4 |
| 6,322,554 B1 | * | 11/2001 | Tomita | 606/4 |
| 6,590,698 B1 | * | 7/2003 | Ohtsuki et al. | 359/326 |

FOREIGN PATENT DOCUMENTS

| | | |
|---|---|---|
| EP | 0 224 322 A1 | 6/1987 |
| EP | 0 765 648 A2 | 9/1996 |
| EP | 1 063 742 A1 | 12/2000 |

(Continued)

*Primary Examiner*—Roy D Gibson
*Assistant Examiner*—Henry M Johnson, III
(74) *Attorney, Agent, or Firm*—Morgan, Lewis & Bockius LLP

(57) ABSTRACT

A laser treatment apparatus is constructed from a [a] laser apparatus 10 equipped with a laser light generating device 11 which has a solid-state laser 12 that generates a specified laser light, a fiber light amplifier 20 that amplifies the laser light generated by this laser light generating device, and a wavelength converter 40 that converts the amplified laser light into treatment laser light with a wavelength of approximately 193 nm using a nonlinear optical crystal, and [b] an irradiation optical device 60 which conducts the treatment laser light generated by this laser apparatus to the surface of the cornea and irradiates the surface of the cornea. As a result, a laser treatment apparatus can be obtained which is especially suitable for treatment of the cornea, and which uses a solid-state laser apparatus that is easy to maintain and that has a compact and light-weight construction.

1 Claim, 12 Drawing Sheets

FOREIGN PATENT DOCUMENTS

| | | |
|---|---|---|
| JP | 05-084314 | 4/1993 |
| JP | 5-220189 | 8/1993 |
| JP | 6-181944 B2 | 7/1994 |
| JP | 6-226471 | 8/1994 |
| JP | 06-233778 | 8/1994 |
| JP | 09-038101 | 2/1997 |
| JP | 09-127566 | 5/1997 |
| TW | 367640 | 8/1999 |
| WO | WO99/46835 | 9/1999 |

* cited by examiner (a)    (b)

LASER TREATMENT APPARATUS

The present application is a continuation of PCT/JP01/03037 filed on Apr. 9, 2001, which was published as WO 01/78632 A1 on Oct. 25, 2001 in Japanese language. In addition, the present application is a Continuation-In-Part of application Ser. No. 09/538,233, filed on Mar. 30, 2000, now U.S. Pat. No. 6,590,698, which is a continuation of PCT/JP98/05367 filed on Nov. 30, 1998.

TECHNICAL FIELD

The present invention relates to a treatment apparatus using laser light, and more specifically relates to a laser treatment apparatus that is suitable for use in the treatment of myopia and astigmatism, etc., by the correction of the curvature or indentations and projections of the cornea through ablation of the surface of the cornea by irradiation with laser light (PRK: photorefractive keratectomy) or ablation of the interior of the cornea in which an incision has been made (LASIK: laser intrastromal keratomileusis).

BACKGROUND ART

In recent years, laser light has been used in various applications, e.g., in the cutting and working of metals, as a light source in the photolithographic apparatus used in semiconductor manufacturing systems, in various types of measuring devices, and in treatment apparatuses and operations performed in the fields of surgery, ophthalmology and dentistry, etc. Recently, the treatment of myopia, hyperopia and astigmatism by the correction of the curvature or indentations and projections of the cornea through ablation of surface of the cornea by irradiation with laser light (PRK) or ablation of the interior of the cornea in which an incision has been made (LASIK) has received particular attention, and such treatment has seen some practical use. An apparatus in which ablation of the surface of the cornea is accomplished by irradiating the cornea with ArF excimer laser light (wavelength: 193 nm) is known as such a cornea treatment apparatus (for example, see Japanese Patent No. 2809959, Japanese Patent Application Kokoku No. H7-121268 and Japanese Patent Application Kokai No. H5-220189).

Ablation of the surface of the cornea using ArF excimer laser light utilizes the fact that the photons with a wavelength of 193 nm that make up ArF laser light have an energy that cuts material bonds such as C—N, C—C, C—O, C—H and C=C bonds, so that such light can break down peptides, which are the basic units of proteins. In this technique, ablation of the surface of the cornea is accomplished by irradiating the surface of the cornea with laser light so that the peptides are broken down and volatilized.

In this case, however, it is necessary to perform precise volatilization in which there is no heat-solidified layer in order to maintain the transparency of the cornea. For this reason, ArF excimer laser light at a wavelength of 193 nm is utilized at which mainly volatilization by the scission of material bonds occurs, with little thermal volatilization taking place. Furthermore, it is also possible to cause volatilization of the surface of the cornea by means of KrF laser light with a longer wavelength (248 nm) or XeCl laser light (wavelength: 308 nm). In such cases, however, the rate of occurrence of thermal volatilization is high in addition to volatilization effected by the scission of material bonds, so that a heat-solidified layer tends to be generated.

Furthermore, the following problem also arises: namely, the DNA inside cells is susceptible to damage when subjected to irradiation with laser light, so that there is a danger that spontaneous mutations will be induced. The absorption spectrum of DNA tends to show larger values at shorter wavelengths of light in the ultraviolet region; however, the effective induction of spontaneous mutations is determined by the quantity of light that passes through the cytoplasm and reaches the nuclei, as well as the absorption of light by the nuclei. The induction of spontaneous mutations is extremely great at wavelengths of 240 to 280 nm, and is lower at wavelengths that are shorter or longer than this range. Especially on the short wavelength side of this range, the absorption of light by the cytoplasm increases abruptly with a decrease in the wavelength. Accordingly, there is an abrupt decrease in the amount of light that reaches the nucleus as the wavelength becomes shorter, so that in the case of light at a wavelength of 193 nm, the amount of light that reaches the nucleus is almost zero. Furthermore, the following problem also arises: namely, light at wavelengths shorter than 193 nm is absorbed during propagation through air, so that the propagation efficiency is low. Judging from such facts, it appears that ArF excimer laser light with a wavelength of 193 nm is most suitable for use in corneal therapy, rather than KrF laser light or XeCl laser light.

However, an ArF excimer laser oscillating apparatus is constructed by sealing argon gas, fluorine gas and neon gas, etc., inside a chamber, and these gases must be tightly sealed. Furthermore, replenishment and recovery of the respective gases must also be performed, so that the apparatus tends to become large and complicated. Furthermore, in order to maintain a specified laser light generating performance in an ArF excimer laser oscillating apparatus, there is a need for periodic overhaul and replacement of the internal gases.

DISCLOSURE OF THE INVENTION

The present invention was devised in light of such problems; the object of the present invention is to provide a laser treatment apparatus using a solid-state laser which allows easy maintenance, and which has a compact and light-weight construction.

In the present invention, in order to achieve such an object, a laser treatment apparatus is constructed from [a] a laser apparatus which is equipped with [i] a laser light generating device having a solid-state laser that generates laser light of a specified wavelength, [ii] a light amplifier that amplifies the laser light generated by this laser light generating device, and [iii] a wavelength converter which uses a nonlinear optical crystal to convert the laser light amplified by the light amplifier into treatment laser light with a wavelength of approximately 193 nm, and [b] an irradiation optical device which conducts the treatment laser light generated by this laser apparatus to the treatment site, and irradiates the treatment site with this treatment laser light. Furthermore, the laser treatment apparatus of the present invention is suitable for use in the treatment of the cornea.

Since the laser treatment apparatus constructed as described above is constructed using a laser light generating device that has a solid-state laser, there is no increase in the size of the apparatus as there is in the case of a gas laser such as an excimer laser, so that a compact and light-weight apparatus construction can be obtained. Furthermore, there is no need for the periodic replacement of gases as there is in the case of an excimer laser apparatus; accordingly, the apparatus of the present invention is characterized by the fact that a specified performance can be maintained over a long period of time without overhaul. Consequently, there is not much need for maintenance, and maintenance is easy. Moreover, control of the operation of the laser light generating device is easy, and control of the irradiation position of the laser light and control of the irradiation intensity, etc., are also easy.

Furthermore, since laser light with a wavelength of approximately 193 nm, which is more or less the same wavelength as that of ArF excimer laser light, is generated, the surface of the cornea can be volatilized through the scission of material bonds by irradiating the surface of the cornea with this laser light, so that the curvature of the cornea and indentations and projections in the cornea can be effectively corrected. In this case, there is little occurrence of thermal volatilization, so that the transparency of the cornea following treatment can be ensured. Furthermore, since the wavelength used is approximately 193 nm, there is no damage to DNA inside cells.

Furthermore, in the laser treatment apparatus of the present invention, it is desirable that the solid-state laser be constructed from a DFB semiconductor laser, a semiconductor laser or a fiber laser which has an oscillation wavelength in the range of 1.51 $\mu$m to 1.59 $\mu$m, and that the apparatus be constructed so that laser light of the above-mentioned wavelength from the solid-state laser is converted into the 8th harmonic with a wavelength in the range of 189 nm to 199 nm by means of a wavelength converter. As a result, the treatment site can be irradiated with laser light that has an extremely high frequency, so that the scission of material bonds at the treatment site can be performed with high efficiency by this laser light, thus making it possible to perform a treatment in which there is little occurrence of thermal volatilization.

In the laser treatment apparatus of the present invention, it is desirable to provide a treatment site observation device which makes it possible to observe the conditions of irradiation of the treatment site by the treatment laser light. As a result, laser irradiation control can be accurately performed while observing the treatment site.

Furthermore, it is desirable to provide an irradiation control device that controls the conditions of irradiation of the treatment site with the treatment laser light by the irradiation optical device. In this case, the apparatus can be constructed so that the irradiation optical device irradiates the treatment site with the treatment laser light as spot-form light, and the irradiation control device can be constructed so that this irradiation control device causes this spot-form light to scan the treatment site. Alternatively, the apparatus can be constructed so that the irradiation optical device broadly irradiates a specified range of the treatment site with the treatment laser light, and the irradiation control device can be disposed between the treatment site and the irradiation optical device and constructed so that this irradiation control device variably adjusts the irradiation region of the treatment laser light with respect to the treatment site. Furthermore, the apparatus can be constructed so that the irradiation optical device broadly irradiates a specified range of the treatment site with the treatment laser light, and the irradiation control device can be disposed between the treatment site and the irradiation optical device and constructed so that this irradiation control device variably adjusts the irradiation intensity of the treatment laser light with respect to the treatment site.

In the present invention, a shape measuring device that measures the shape of the treatment site can be provided, and the apparatus can be constructed so that the irradiation control of the treatment laser light performed by the irradiation control device is performed on the basis of the shape of the treatment site measured by the shape measuring device. As a result, the treatment of myopia, hyperopia and astigmatism, etc., can be accurately performed in accordance with the degree of the disorder.

In the present invention, furthermore, an intensity adjustment device that adjusts the intensity of the treatment laser light generated by the above-mentioned laser apparatus may be installed in the laser apparatus. Furthermore, it would also be possible to install a laser light intensity measuring device that measures the intensity of the treatment laser light generated by the laser apparatus, and a laser light intensity correction device that corrects the intensity of the treatment laser light measured by the laser light intensity measuring device to a specified intensity. As a result, accurate treatment can be maintained by always maintaining the laser light intensity at an appropriate value.

Furthermore, it is desirable to use pulsed light as the treatment laser light that is generated by the laser apparatus, and the pulse width of the pulsed light in this case is preferably set at 0.5 ns to 3 ns. Furthermore, it is desirable that the repetition frequency of this pulsed light be set at 10 kHz to 100 kHz.

PREFERRED WORKING CONFIGURATIONS OF THE INVENTION

Preferred working configurations of the present invention will be described below with reference to the attached figures; however, the description of these working configurations does not limit the content of the present invention.

Figure 1:
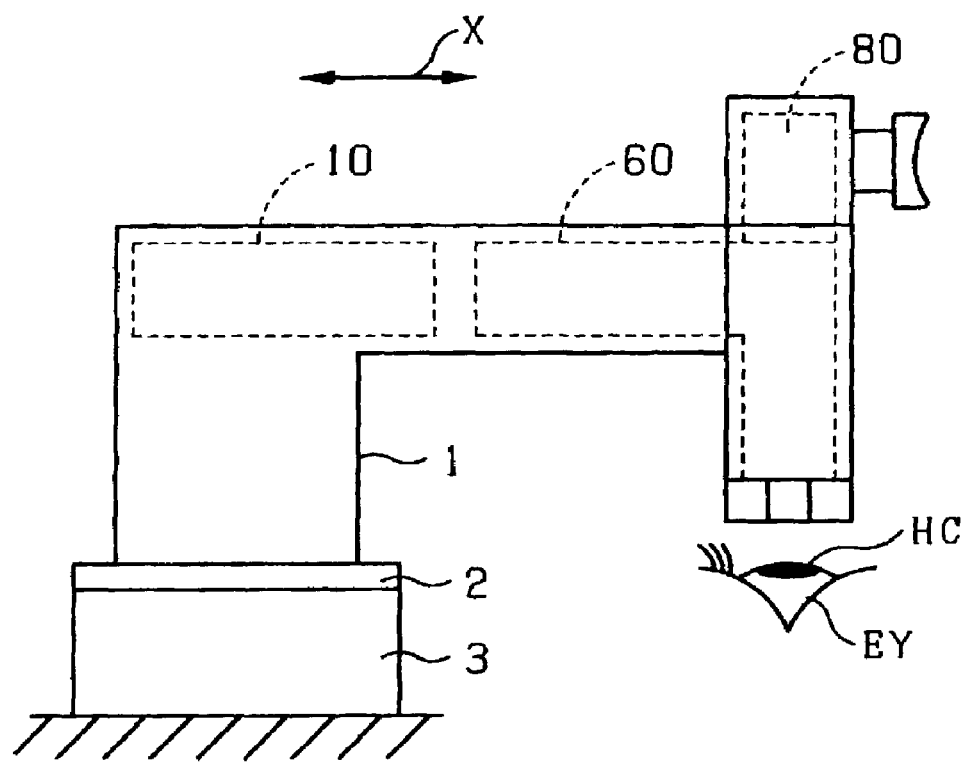
FIG. 1 is a front view which shows the overall construction of the laser treatment apparatus of the present invention.

An example of the overall construction of the laser treatment apparatus of the present invention is shown in FIG. 1. This laser treatment apparatus is basically constructed by installing a laser apparatus 10, an irradiation optical device 60 which conducts the laser light generated by this laser apparatus 10 to the surface of the cornea HC of the eyeball EY (i.e., the treatment site) and irradiates this surface with this laser light, and an observation optical device 80 that is used to observe the treatment site, inside an apparatus housing 1. The base part 2 of the apparatus housing 1 is disposed on an X-Y moving table 3, and the apparatus housing 1 as a whole can be moved in the direction indicated by the arrow X in FIG. 1, i.e., in the left-right direction of the figure, and in the Y direction perpendicular to the plane of the page, by means of the X-Y moving table 3.

Figure 2:
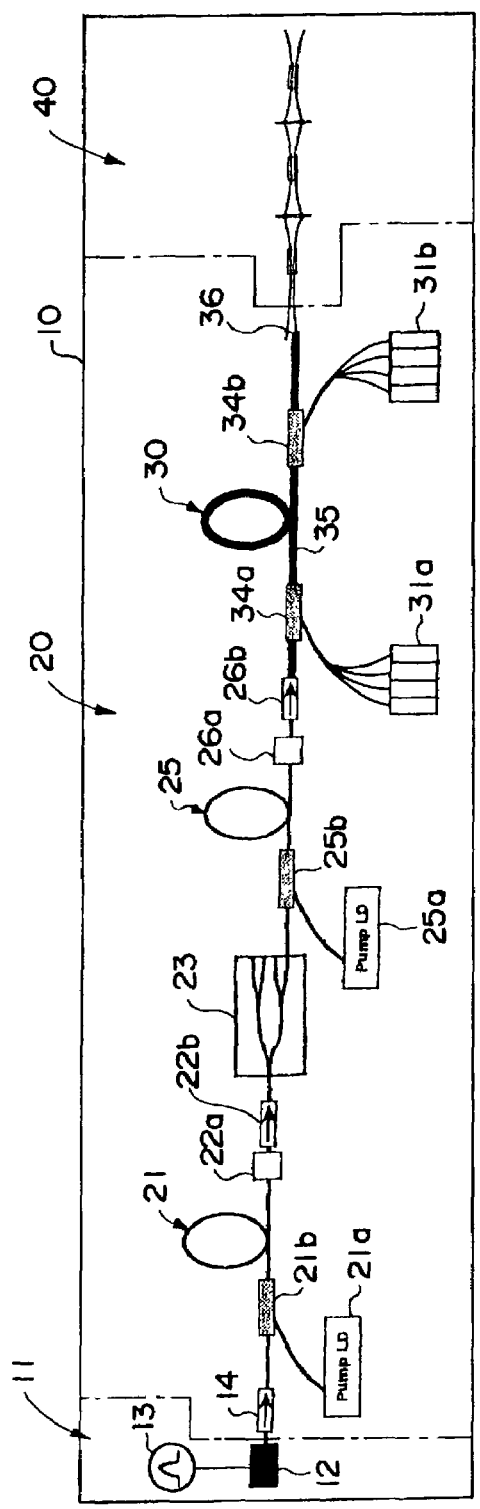
FIG. 2 is an explanatory diagram which shows the internal construction of the laser apparatus that forms a part of the above-mentioned laser treatment apparatus.

First, the laser apparatus 10 will be described with reference to FIG. 2. The laser apparatus 10 is constructed from a laser light generating part 11 that generates laser light, a fiber light amplifier part 20 that amplifies the laser light generated by the laser light generating part 11, and a wavelength conversion part 40 that converts the laser light amplified by the fiber light amplifier part 20 into laser light with a wavelength of approximately 193 nm.

The laser light generating part 11 has a laser 12 that oscillates at the desired wavelength; this laser 12 is constructed from (for example) a pulse-driven InGaAsP DFB semiconductor laser with an oscillation wavelength of 1.544 $\mu$m.

For example, in cases where a DFB semiconductor laser is used as the laser, control of the oscillation wavelength of the laser light can be achieved by controlling the temperature of the DFB semiconductor laser. The oscillation wavelength can be further stabilized and controlled to a constant wavelength, or the output wavelength can be finely adjusted, using this method.

Ordinarily, DFB semiconductor lasers, etc., are installed on a heat sink, and these parts are accommodated inside a housing. In the present example, a temperature adjustment device (e.g., a Peltier element, etc.) which is disposed on a heat sink attached to the oscillating laser (DFB semiconductor laser, etc.) 12 is used to control the temperature and adjust the oscillation wavelength. Here, in the case of a DFB semiconductor laser, etc., the temperature can be controlled in units of 0.001° C.

Furthermore, the oscillation wavelength of a DFB semiconductor laser has a temperature dependence of approximately 0.1 nm/° C. For example, if the temperature of a DFB semiconductor laser is varied by 1° C., the wavelength varies by 0.1 nm in the case of the fundamental wave (wavelength: 1544 nm); therefore, the wavelength varies by 0.0125 nm in the case of the 8th-harmonic wave (wavelength: 193 nm).

Furthermore, as for the monitoring wavelength used for feedback control when this oscillation wavelength is controlled to a specified wavelength, this is accomplished using the oscillation wavelength of the DFB semiconductor laser. In this semiconductor laser 12, a pulse control means 13 is provided which causes a pulsed oscillation by performing current control, etc. As a result, the pulse width of the pulsed light that is created can be controlled within a range of 0.5 ns to 3 ns, and the repetition frequency can be controlled within a range of 100 kHz or less (e.g., a range of 10 kHz to 100 kHz). In the present construction, as one example, pulsed light with a pulse width of 1 ns and a repetition frequency of 100 kHz is created by the pulse control means 13.

The pulsed laser light output thus obtained passes through an optical isolator 14, and is conducted into a fiber light amplifier part 20; the laser light is amplified in this fiber light amplifier part 20. In this fiber light amplifier part 20, amplification is first performed by a first-stage fiber light amplifier 21. This first-stage fiber light amplifier 21 is constructed from an erbium (Er) doped fiber light amplifier (EDFA). The output from a semiconductor laser 21a used for excitation passes through a wavelength division multiplexer (WDM) 21b so that the doped fiber is excited, and light amplification is thus performed by the first-stage fiber light amplifier 21.

The output of the first-stage fiber light amplifier 21 passes through a narrow-band filter 22a and an optical isolator 22b, and is conducted to a light splitter 23. The light is divided in parallel into four outputs of channels 0 through 3 by the light splitter 23. A second-stage fiber light amplifier 25 is connected for each channel resulting from this four-way split. However, in FIG. 2, only one channel is shown as a representative example.

Furthermore, the narrow-band filter 22a cuts the ASE light generated by the fiber light amplifier 21, and allows the output wavelength of the DFB semiconductor laser 12 (with a wavelength width of approximately 1 pm or less) to pass through, so that the wavelength width of the transmitted light is substantially narrowed. As a result, the ASE light can be prevented from entering the later-stage fiber light amplifiers and lowering the amplification gain of the laser light. Here, it is desirable that the transmission wavelength width of the narrow-band filter be approximately 1 pm; however, since the wavelength width of the ASE light is several tens of nanometers, the ASE light can be sufficiently cut so that there is no practical problem even if a narrow-band filter with the currently obtainable transmission wavelength width of approximately 100 pm is used. In cases where the output wavelength of the DFB semiconductor laser 12 is deliberately varied, the narrow-band filter may be replaced in accordance with the output wavelength. However, it is desirable to use a narrow-band filter which has a transmission wavelength width that corresponds to (i.e., that is comparable to or greater than) the variable width of the output wavelength (as one example in an exposure apparatus, approximately the above-mentioned ±20 pm).

In the above construction, an example was described in which a DFB semiconductor laser was used as the laser, and a flat-plate waveguide-type splitter was used as the branching element of the light branching means. However, any laser that oscillates at the desired wavelength may be used as the laser light source; for example, a similar effect can be obtained using an erbium (Er) doped fiber laser. Furthermore, any element that causes the parallel branching of light in the same manner as a flat-plate waveguide splitter may be used as the branching element of the light branching means; for example, a similar effect can also be obtained using a fiber splitter or a beam splitter that uses a partially transmitting mirror.

The second-stage fiber light amplifiers 25 are also each constructed from an erbium (Er) doped fiber light amplifier (EDFA). The output from a semiconductor laser 25a used for excitation passes through a WDM 25b so that the doped fiber is excited, and light amplification is thus performed by the second-stage fiber light amplifier 25. The output of each second-stage fiber light amplifier 25 is conducted to a third-stage fiber light amplifier 30 via a narrow-band filter 26a and an optical isolator 26b.

This third-stage fiber light amplifier 30 is a device that performs the final stage of light amplification, and constitutes a high-peak output light amplifier. Accordingly, in order to avoid an increase in the spectral width of the amplified light caused by nonlinear effects in the fiber, it is desirable to use a large-mode-diameter fiber light amplifier which has a fiber mode diameter that is broader than that ordinarily used in communications (5 to 6 $\mu$m), e.g., a fiber mode diameter of 15 to 25 $\mu$m.

Figure 3:
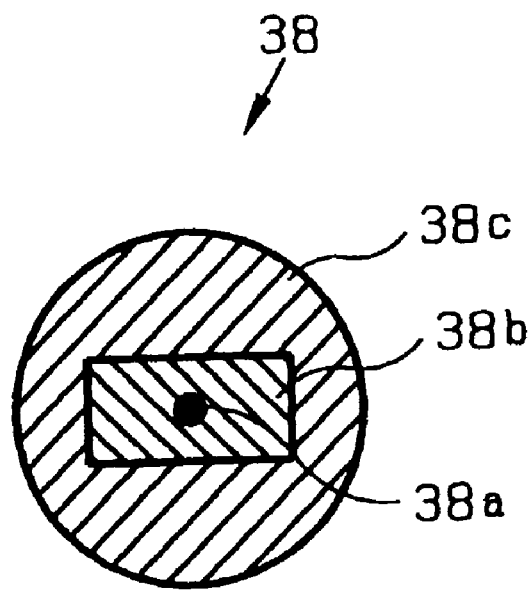
FIG. 3 is a sectional view which shows the construction of the double-clad fiber used in the third-stage fiber light amplifier that forms a part of the above-mentioned laser apparatus.

Furthermore, in order to obtain a high output in the third-stage fiber light amplifier 30, it would also be possible to use a double clad fiber 38 in which the fiber cladding has a double structure instead of the large-mode-diameter fiber 35. One example of a sectional view of this fiber 38 is shown in FIG. 3. In this structure, the core portion 38a is doped with ions that contribute to the amplification of the laser light, so that the amplified laser light (signal) propagates through this core. A semiconductor laser used for excitation is coupled with the first cladding 38b that is wrapped around this core. This first cladding 38b is a multi-mode cladding, and also has a large cross-sectional area; accordingly, the conduction of a high output of semiconductor laser light used for excitation is easy, and a semiconductor laser with multi-mode oscillation can be efficiently coupled, so that the excitation light source can be efficiently used. A second cladding 38c which is used to form a waveguide for the first cladding is formed on the outer circumference of the first cladding 38b.

The laser light amplified by the third-stage fiber light amplifier 30 using this large-mode-diameter fiber enters a wavelength conversion part 40; here, the wavelength is converted to that of ultraviolet laser light with a wavelength of approximately 193 nm, which is the same as the wavelength of excimer laser light. It is desirable that the laser light (signal) that is to be amplified, which propagates through this large-mode-diameter fiber, consist mainly of the fundamental mode; this can be realized by selectively exciting mainly the fundamental mode in a single-mode fiber or a multi-mode fiber that has a low mode order number. The effects of return light are reduced by an isolator 26b installed on the entry side of the large-mode-diameter fiber light amplifier 30.

Furthermore, a narrow-band filter 26a is installed between each second-stage fiber light amplifier 25 (which has a standard mode diameter) and large-mode-diameter (third-stage) fiber light amplifier 30 in order to eliminate the ASE light that is generated by the third-stage fiber light amplifier 30.

The connection of each pre-stage fiber light amplifier 25 which has a standard mode diameter with the corresponding final-stage fiber light amplifier 30 having the above-mentioned expanded mode diameter is accomplished using fibers in which the mode diameter increases in a tapered shape.

Quartz fibers or silicate-type fibers may be used as the optical fibers of the above-mentioned fiber light amplifiers 21, 25 and 30; in addition, fluoride fibers, e.g., ZBLAN fibers, may also be used. In the case of such fluoride fibers, the erbium doping concentration can be increased compared to that in quartz or silicate-type fibers, etc.; as a result, the fiber length necessary for amplification can be shortened.

It is especially desirable that such fluoride-type fibers be used in the final-stage fiber light amplifiers 30. As a result of the shortening of the fiber length, the light scattering (e.g., stimulated Raman scattering) caused by nonlinear effects in the fiber propagation of the pulsed light can be suppressed, so that pulse amplification with a light peak power that maintains the desired wavelength can be accomplished.

In cases where a value of 1.51 to 1.59 $\mu$m is used as the output wavelength of the fiber light amplifiers that have a cladding with a double structure as described above, it is desirable that the fibers be doped with ytterbium in addition to erbium as the doping ions. The reason for this is that such doping has the effect of improving the excitation efficiency of the semiconductor laser. Specifically, in cases where the fibers are doped with both erbium and ytterbium, the strong absorption wavelength of ytterbium is spread in the vicinity of 915 to 975 nm, so that a plurality of semiconductor lasers with various differing oscillation wavelengths in the vicinity of this wavelength range can be coupled by WDM, and can thus be coupled to the first cladding. Since such a plurality of semiconductor lasers can be used as exciting light, a large excitation strength can be realized.

Furthermore, in regard to the design of the doped fibers of the fiber light amplifiers, in the case of an apparatus that operates at a fixed wavelength that is determined in advance as in the present invention, the material of the doped fibers is selected so that the gain of the fiber light amplifiers at the desired wavelength is large. In the present invention, an output wavelength which is the same as that of an ArF excimer laser (193 to 194 nm) is obtained; in the case of such an apparatus, it is desirable to select a material which is such that the gain is large at the desired wavelength, e.g., 1.548 $\mu$m, when light amplifier fibers are used.

Figure 4:
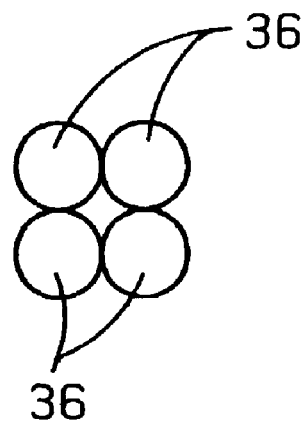
FIG. 4 is a side view which shows the shape of the output terminal part of the third-stage fiber light amplifier that forms a part of the above-mentioned laser apparatus.
Figure 4:
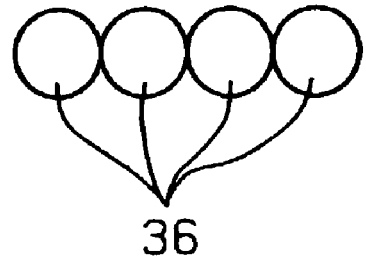
Figure 5:
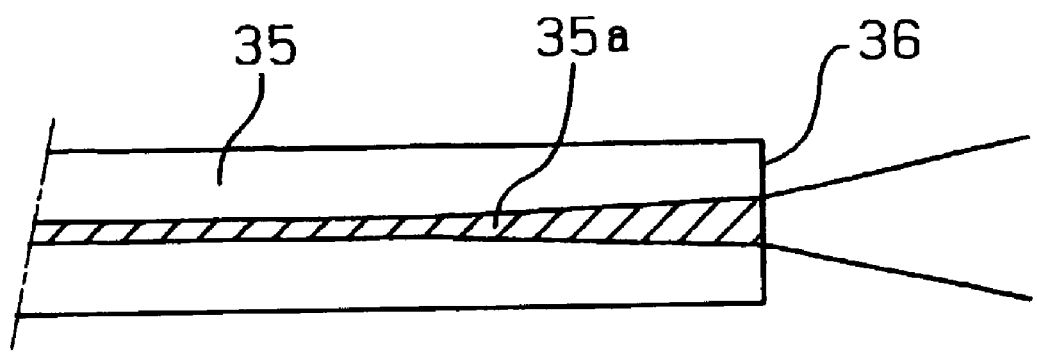
FIG. 5 is a sectional view which shows the shape of the output terminal part of the third-stage fiber light amplifier that forms a part of the above-mentioned laser apparatus.

At the output ends 36 of the third-stage, i.e., final-stage, fiber light amplifiers 30, all four channels are gathered together and bundled, and as is shown in FIG. 4, these channels are molded into a rectangular shape or rectilinear shape (see FIG. 4 (a) or FIG. 4 (b)). Furthermore, as is shown in FIG. 5, at the output end portions 36 of the respective fibers 35 of the final stage in the light amplifiers, it is desirable that the diameters of the cores 35a inside the fibers 35 be gradually expanded in a tapered shape toward the output end, so that the power density of the light (light intensity per unit area) is reduced at the output end surfaces 36. In this case, the shape of the taper is set so that the expansion of the core diameter is sufficiently gradual toward the output end surface 36, thus making it possible to preserve the lateral mode of propagation through the fibers when the amplified laser light propagates through the tapered parts, so that the excitation of other lateral modes is small enough to be ignored (e.g., a few mrad).

By setting the core diameter in this manner, it is possible to lower the power density of the light at the output end surfaces 36 of the fibers, so that damage to the output end portions of the fibers caused by the laser light, which presents the greatest problem in terms of fiber damage, can be greatly suppressed. In regard to this effect, a greater effect is obtained as the power density of the laser light that is emitted from the output ends of the fiber light amplifiers increases (e.g., as the light intensity increases, or as the core diameter relative to the same power decreases).

Furthermore, in the respective working configurations described above, examples were shown of a construction in which appropriate isolators, etc., were inserted into the respective connecting parts in order to avoid the effects of return light, and narrow-band filters were inserted in order to obtain good EDFA amplification characteristics. However, the numbers and locations of such isolators or narrow-band filters are not limited to those shown in the above-mentioned working configurations; for example, such numbers and locations can be appropriately determined in accordance with the required precision of the laser treatment apparatus of the present invention, and either the isolators or narrow-band filters may be completely omitted in some cases.

Furthermore, in the case of the narrow-band filters, it is sufficient if a high transmissivity is obtained only for the desired wavelength; a filter transmission wavelength width of 1 pm or less is sufficient. By thus using narrow-band filters, it is possible to alleviate the noise caused by the spontaneously emitted light ASE (amplified spontaneous emission) that is generated by the fiber light amplifiers. Furthermore, the drop in the amplification rate of the fundamental wave output that is caused from ASE from the pre-stage fiber light amplifier can be suppressed.

Figure 6:
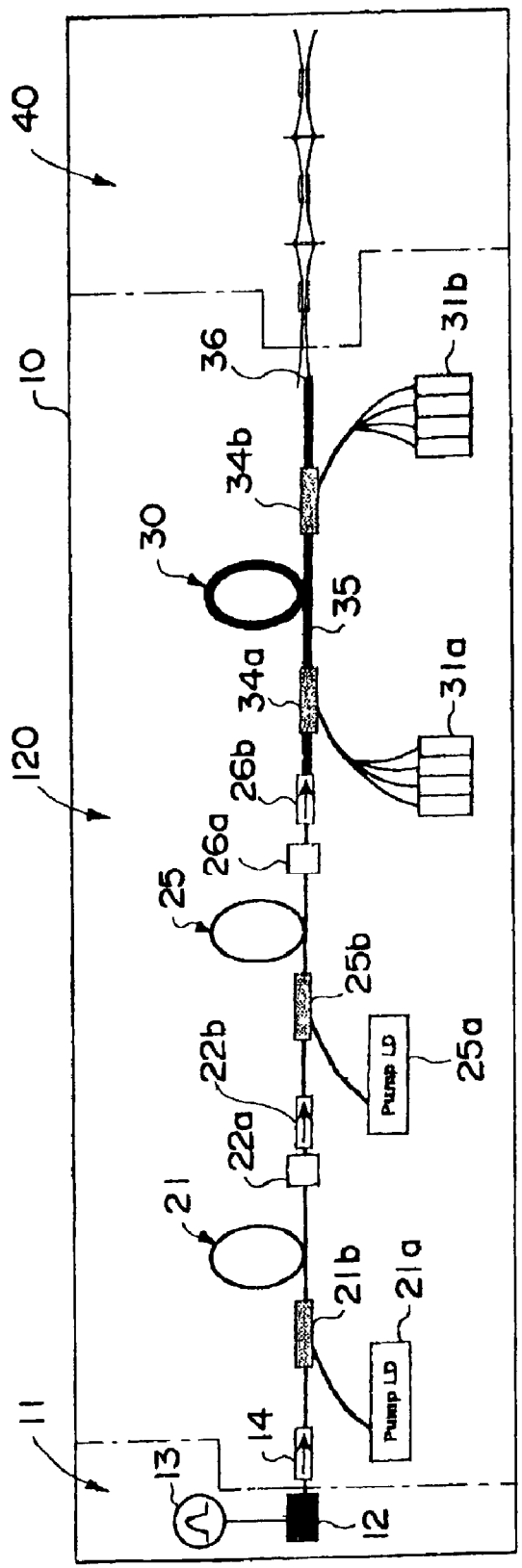
FIG. 6 is an explanatory diagram which shows the internal construction of a different working configuration of the laser apparatus that forms a part of the above-mentioned laser treatment apparatus.

In the above construction, an example was shown in which the light was branched into four rows by a splitter. However, it would also be possible to construct the apparatus using a single row of fiber amplifiers without using a splitter as shown in FIG. 6. In FIG. 6, no splitter is installed between the optical isolator 22b and WDM 25b in the fiber light amplifier 120.

The pulsed light with a wavelength of 1.544 $\mu$m that is thus amplified by the fiber light amplifiers 20 and 120 and output from the output end 36 is converted into an ultraviolet pulsed output with a narrow spectral line width in the wavelength conversion part 40 using a nonlinear optical crystal. The construction of this wavelength conversion part 40 will be described below.

Figure 7:
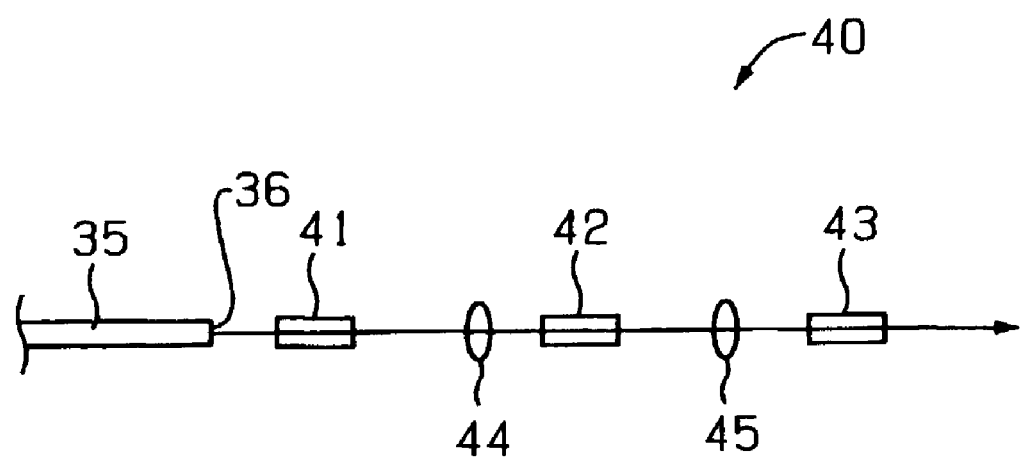
FIG. 7 is an explanatory diagram which shows a first working configuration of the wavelength conversion part that forms a part of the above-mentioned laser treatment apparatus.

FIG. 7 shows a first working configuration of the wavelength conversion part 40; here, an example of a construction is shown in which the fundamental wave with a wavelength of 1.544 $\mu$m that is emitted from the output end 36 of the fiber 35 is converted into the 8th-harmonic wave using a nonlinear optical crystal, thus generating ultraviolet light with a wavelength of 193 nm, which is the same as that of an ArF excimer laser. The fundamental wave with a wavelength of 1.544 $\mu$m (frequency $\omega$) that is output from the output end 36 of the fiber 35 is output from the left to the right in the figure via nonlinear optical crystals 41, 42 and 43. Furthermore, focusing lenses 44 and 45 are disposed between the nonlinear optical crystals 41, 42 and 43 as shown in the figure.

When the fundamental wave passes through the nonlinear optical crystal 41, a 2nd-harmonic wave with a frequency that is twice the frequency $\omega$ of the fundamental wave, i.e., a frequency of 2$\omega$ (with a wavelength of ½ the original wavelength, i.e., 772 nm) is generated as a result of the generation of the second harmonic frequency. The 2nd-harmonic wave thus generated advances to the right, and enters the next nonlinear optical crystal 42. Here, a second harmonic frequency is again generated, so that a 4th-harmonic wave is generated which has a frequency that is twice the frequency 2$\omega$ of the incident wave, i.e., a frequency of 4$\omega$ (with a wavelength of ¼ the original wavelength; i.e., 386 nm) that is four times the frequency of the fundamental wave. The 4th-harmonic wave thus generated advances into the nonlinear optical crystal 43 located still further to the right; here, a second harmonic is again generated, so that an 8th-harmonic wave is generated which has a frequency of 8$\omega$ (with a wavelength of ⅛ the original wavelength, i.e., 193 nm) that is twice the frequency 4$\omega$ of the incident wave, i.e., eight times the frequency of the fundamental wave.

In regard to the nonlinear optical crystals used for the above-mentioned wavelength conversion, for example, an $LiB_3O_5$ (LBO) crystal is used as the nonlinear optical crystal 41 that performs the conversion from the fundamental wave to the 2nd-harmonic wave, an $LiB_3O_5$ (LBO) crystal is used as the nonlinear optical crystal 42 that performs the conversion from the 2nd-harmonic wave to the 4th-harmonic wave, and an $Sr_2Be_2B_2O_7$ (SBBO) crystal is used as the nonlinear optical crystal 43 that performs the conversion from the 4th-harmonic wave to the 8th-harmonic wave. Here, a method that depends on the temperature adjustment of the LBO crystal, i.e., non-critical phase matching (NCPM), is used for the wavelength conversion phase matching in the conversion from the fundamental wave to the 2nd-harmonic wave using the LBO crystal. In the case of NCPM, there is no angular deviation (walk-off) between the fundamental wave and the second harmonic inside the nonlinear optical crystal. Accordingly, conversion to the 2nd-harmonic wave can be performed with a high efficiency. Furthermore, the 2nd-harmonic wave that is generated is not subjected to beam deformation caused by walk-off; accordingly, such a method is advantageous.

Figure 8:
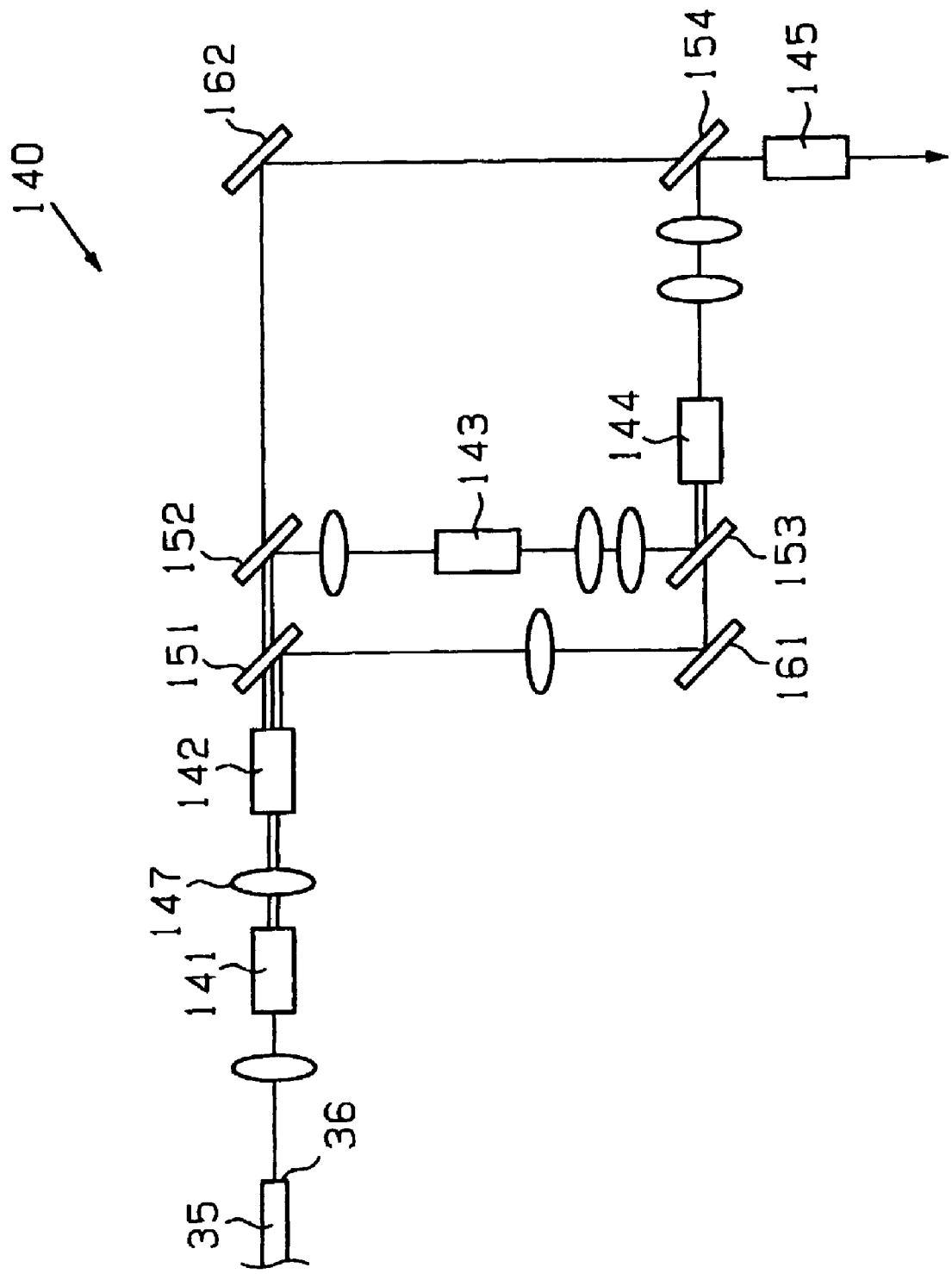
FIG. 8 is an explanatory diagram which shows a second working configuration of the wavelength conversion part that forms a part of the above-mentioned laser treatment apparatus.

The wavelength conversion part is not limited to the above-mentioned construction; various constructions may be used. For example, a construction of the wavelength conversion part 140 according to a second working configuration is shown in FIG. 8. In this wavelength conversion part, wavelength conversion is performed in the following order: fundamental wave (wavelength 1.544 $\mu$m)→2nd-harmonic wave (wavelength 772 nm)→3rd-harmonic wave (wavelength 515 nm)→4th-harmonic wave (wavelength 386 nm)→7th-harmonic wave (wavelength 221 nm)→8th-harmonic wave (wavelength 193 nm).

In the first wavelength conversion part 141, an LBO crystal is used for the second harmonic conversion of the fundamental wave into a 2nd-harmonic wave by the above-mentioned NCPM. The first wavelength conversion part (LBO crystal) 141 allows a portion of the fundamental wave to pass through without wavelength conversion, and also generates a 2nd-harmonic wave by wavelength conversion of the fundamental wave, so that this fundamental wave and 2nd-harmonic wave both enter the second wavelength conversion part 142.

In the second wavelength conversion part 142, a 3rd-harmonic wave (frequency 515 nm) is obtained by the generation of a sum frequency from the 2nd-harmonic wave generated by the first wavelength conversion part 141 and the fundamental wave that passed through without conversion. An LBO crystal is used as the wavelength converting crystal; however, this crystal is used in NCPM in which the temperature differs from that of the first wavelength conversion part (LBO crystal) 141. The 3rd-harmonic wave thus obtained, and the 2nd-harmonic wave and fundamental wave that have passed through without wavelength conversion, are separated by a first dichroic mirror 151. The 3rd-harmonic wave reflected by the first dichroic mirror 151 passes through a lens and is reflected by a fully reflective mirror 161; this 3rd-harmonic wave is then incident on a third dichroic mirror 153.

Meanwhile, the 2nd-harmonic wave and fundamental wave that have passed through the first dichroic mirror 151 are separated by a second dichroic mirror 152. The 2nd-harmonic wave that is reflected by the second dichroic mirror 152 is converted into a 4th-harmonic wave which has a frequency of 4ω (with a wavelength of ¼ the original wavelength, i.e., 386 nm) that is twice the frequency 2ω of the incident wave, i.e., four times the frequency of the fundamental wave, by the third wavelength conversion part 143 using an LBO crystal. This 4th-harmonic wave is reflected by the third dichroic mirror 153, and is then reflected by a fully reflective mirror 161 and caused to be incident on the fourth wavelength conversion part 144 (using a BBO crystal) together with the 3rd-harmonic wave that has passed through the third dichroic mirror 153. In this fourth wavelength conversion part 144, a 7th-harmonic wave is formed by generating the sum frequency of the incident 3rd-harmonic wave and 4th-harmonic wave, and this 7th-harmonic wave is caused to be incident on a fourth dichroic mirror 154.

Furthermore, the fundamental wave that has passed through the second dichroic mirror 152 is reflected by a second fully reflective mirror 162, and is then caused to be incident on the fourth dichroic mirror 154. The 7th-harmonic wave and fundamental wave that are thus caused to be incident on the fourth dichroic mirror 154 enter the fifth wavelength conversion part 145 using a CLBO crystal. In the fifth wavelength conversion part 145, an 8th-harmonic wave is formed by generating the sum frequency of the incident fundamental wave and 7th-harmonic wave, and this 8th-harmonic wave is output as the output laser light.

Figure 9:
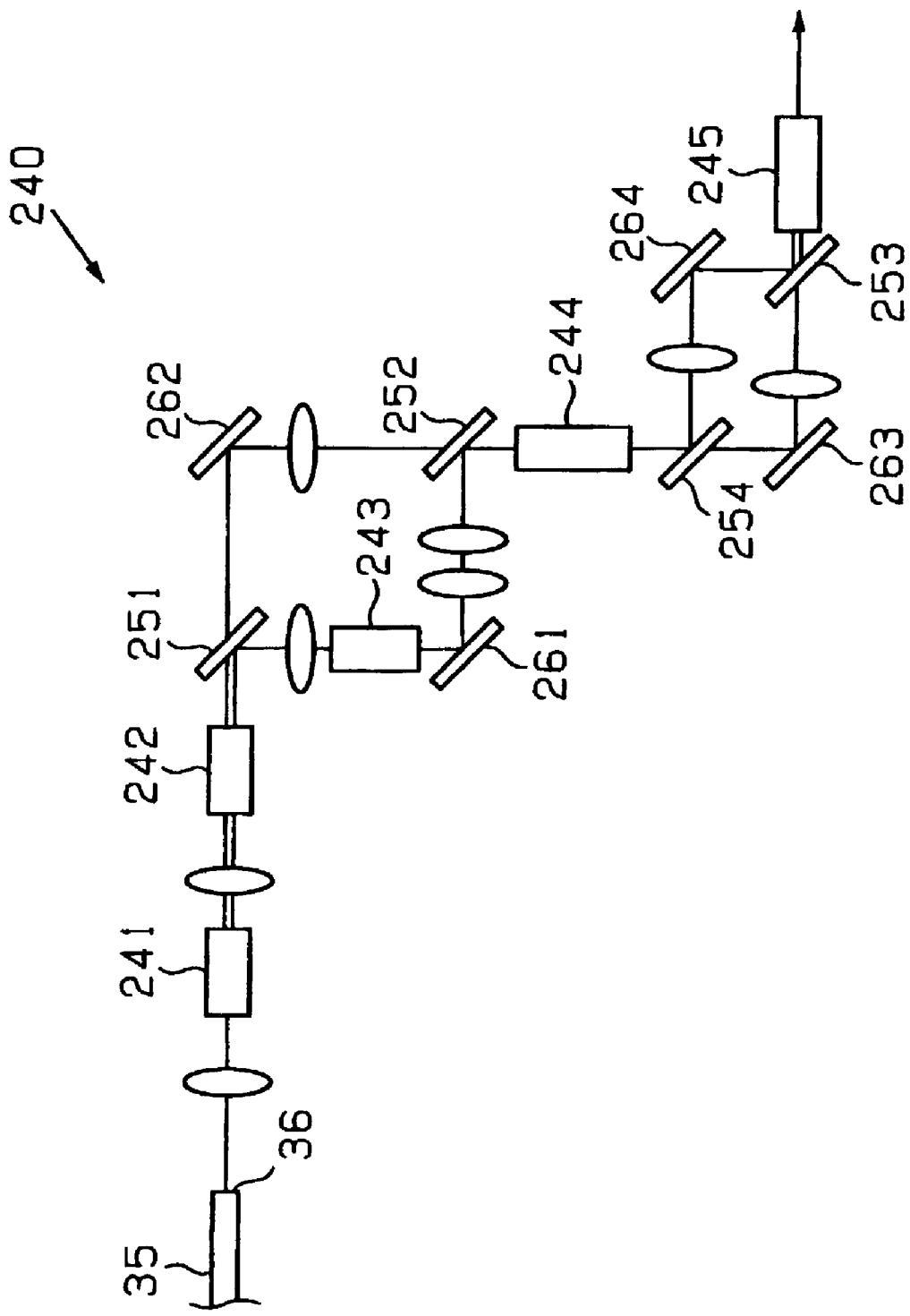
FIG. 9 is an explanatory diagram which shows a third working configuration of the wavelength conversion part that forms a part of the above-mentioned laser treatment apparatus.

FIG. 9 shows the construction of the wavelength conversion part 240 of a third working configuration. In this wavelength conversion part, wavelength conversion is performed in the following order: fundamental wave (wavelength 1.544 μm)→2nd-harmonic wave (wavelength 772 nm)→3rd-harmonic wave (wavelength 515 nm)→6th-harmonic wave (wavelength 257 nm)→7th-harmonic wave (wavelength 221 nm)→8th-harmonic wave (wavelength 193 nm).

In the first wavelength conversion part 241, an LBO crystal is used for the second harmonic conversion of the fundamental wave into a 2nd-harmonic wave by the above-mentioned NCPM. The first wavelength conversion part (LBO crystal) 241 allows a portion of the fundamental wave to pass through without wavelength conversion, and generates a 2nd-harmonic wave by converting the wavelength of the fundamental wave; this fundamental wave and 2nd-harmonic wave both enter the second wavelength conversion part 242.

In the second wavelength conversion part 242, a 3rd-harmonic wave (wavelength 515 nm) is obtained by generating the sum frequency of the 2nd-harmonic wave generated by the first wavelength conversion part 241 and the fundamental wave that has passed through without conversion. An LBO crystal is used as the wavelength converting crystal; however, this crystal is used in NCPM in which the temperature differs from that of the first wavelength conversion part (LBO crystal) 241. The 3rd-harmonic wave thus obtained, and the fundamental wave that has passed though without being subjected to wavelength conversion, are separated by a first dichroic mirror 251. The 3rd-harmonic wave that is reflected by the first dichroic mirror 251 enters the third wavelength conversion part 243 (using a BBO crystal), and is converted into a 6th-harmonic wave here. This 6th-harmonic wave is reflected by a first fully reflective mirror 261, and is caused to be incident on a second dichroic mirror 252.

Meanwhile, the fundamental wave that has passed through the first dichroic mirror 251 is reflected by a second fully reflective mirror 262 and is caused to be incident on the second dichroic mirror 252. The 6th-harmonic wave and fundamental wave that are thus caused to be incident on the second dichroic mirror 252 are conflated by the second dichroic mirror 252 and caused to enter the fourth wavelength conversion part 244 using a CLBO crystal. In the fourth wavelength conversion part 244, the 6th-harmonic wave and fundamental wave that are thus caused to be incident are synthesized to form a 7th-harmonic wave, and a portion of the fundamental wave is allowed to pass through "as is." The 7th-harmonic wave that is thus output from the fourth wavelength conversion part 244 is reflected by a dichroic mirror 254, and the fundamental wave passes through the dichroic mirror 254. Then, after being respectively focused by lenses, these waves are conflated by a third dichroic mirror 253, and caused to enter the fifth wavelength conversion part 245 using a CLBO crystal, where the waves are synthesized so that an 8th-harmonic wave is formed. This 8th-harmonic wave is output as the output laser light.

Furthermore, in the respective examples shown in FIGS. 7 through 9 above, optical lenses are disposed as shown in the figures. Furthermore, wavelength plates may be appropriately disposed in order to adjust the direction of polarization to the desired direction. Moreover, the construction of the wavelength conversion part is not limited to the constructions described above; any construction that generates an 8th-harmonic wave of the 1.544 μm fundamental wave may be used. For example, a similar effect can be obtained by wavelength conversion in the following order: fundamental wave (wavelength 1.544 μm)→2nd-harmonic wave (wavelength 772 nm)→3rd-harmonic wave (wavelength 515 nm)→4th-harmonic wave (wavelength 386 nm)→6th-harmonic wave (wavelength 257nm)→7th-harmonic wave (wavelength 221 nm)→8th-harmonic wave (wavelength 193 nm).

In regard to the nonlinear optical crystals that are used for wavelength conversion in this case, this conversion can be achieved (for example) by using an LBO crystal as the crystal that converts the fundamental wave into a 2nd-harmonic wave, an LBO crystal as the crystal that converts the 2nd-harmonic wave into a 4th-harmonic wave, a BBO crystal as the crystal that generates a 6th-harmonic wave by generating the sum frequency of the 2nd-harmonic wave and 4th-harmonic wave, a BBO crystal as the crystal that generates a 7th-harmonic wave by generating the sum frequency of the fundamental wave and the 6th-harmonic wave, and an LBO crystal as the crystal that generates an 8th-harmonic wave by generating the sum frequency of the fundamental wave and the 7th-harmonic wave. In this case as well, an LBO crystal can be used to generate the 8th-harmonic wave; accordingly, this method is advantageous in that crystal damage is not a problem.

Examples in which wavelength conversion was performed using a single row of fibers were described above; however, a similar method is used in the case of bundles, and lens arrays, etc., that allow bundle wavelength conversion are used in the lens parts.

Next, an irradiation optical device 60 and observation optical device 80 will be described in which laser light with the same 193 nm wavelength as ArF excimer laser light, which is generated by a laser apparatus 10 constructed as described above, is conducted to the surface of the cornea HC of the eyeball EY and caused to irradiate this surface. Furthermore, in the laser apparatus 10, as was described above, the solid-state laser is constructed from a DFB semiconductor laser or fiber laser that has an oscillation wavelength in the range of 1.51 μm to 1.59 μm; accordingly, the laser light of the above-mentioned wavelength from the solid-state laser is converted into laser light that has an octuple harmonic frequency in the range of 189 nm to 199 nm by the wavelength converter, and this laser light is output. Thus, this laser light is laser light of substantially the same wavelength as ArF excimer laser light; however, the repetition frequency of the pulsed oscillation is extremely high, i.e., 100 kHz.

Figure 10:
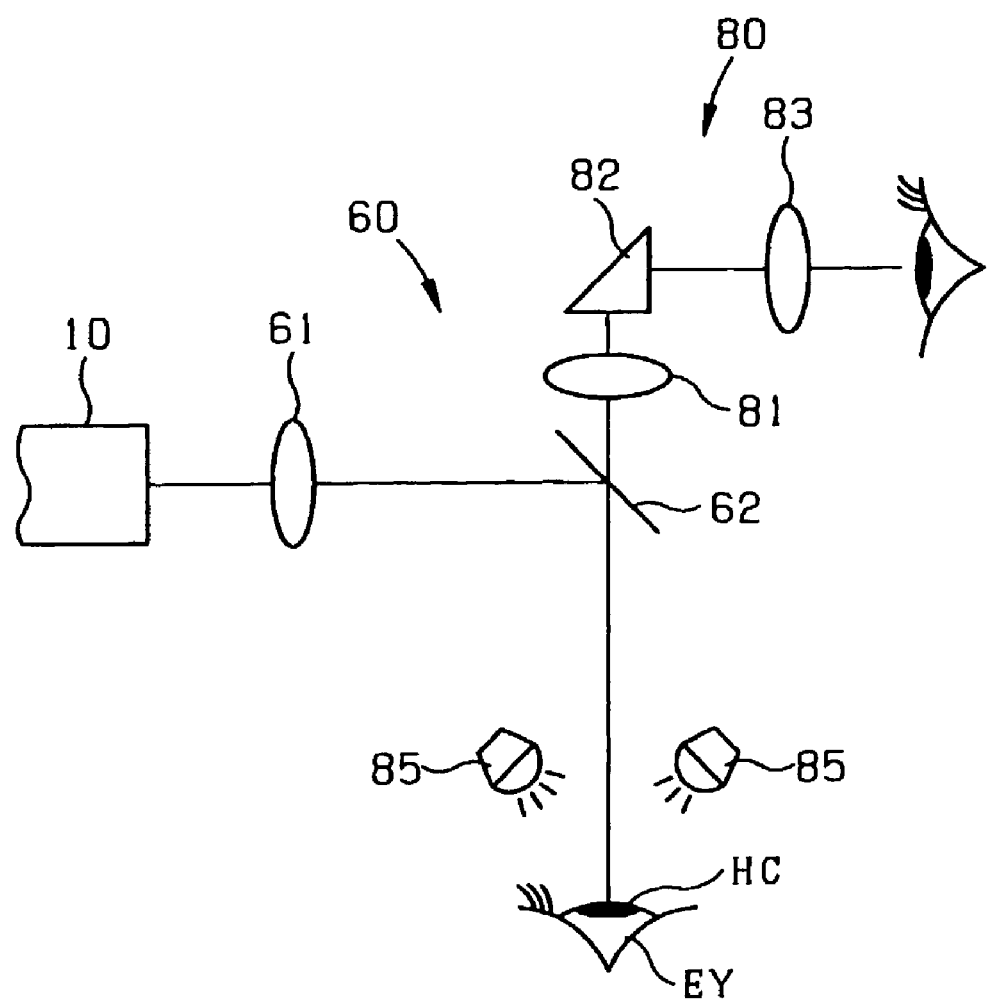
FIG. 10 is an explanatory diagram which shows the construction of a first working configuration of the irradiation optical device and observation optical device that form parts of the above-mentioned laser treatment apparatus.

A first working configuration of this irradiation optical device 60 and observation optical device 80 is shown in FIG. 10. The irradiation optical device 60 is constructed from a focusing lens 61 that focuses the laser light with a wavelength of 193 nm that is emitted from the above-mentioned laser apparatus 10 into the form of a slender beam, and a dichroic mirror 62 that reflects this focused beam-form laser light so that this laser light is caused to irradiate the surface of the cornea HC of the eyeball EY that constitutes the object of treatment. As a result, the surface of the cornea HC is irradiated with the laser light as spot-form light, and this portion of the cornea is volatilized. In this case, the laser light spot that is directed onto the surface of the cornea HC is caused to perform a scanning movement by using the X-Y moving table 3 to move the apparatus housing 1 as a whole in the X and Y directions, so that the surface of the cornea is ablated, thus treating myopia, hyperopia or astigmatism, etc.

Such a treatment is performed by controlling the operation of the X-Y moving table 3 while the person performing the operation (such as an ophthalmologist, etc.) visually observes the operation via the observation optical device 80. This observation optical device 80 is constructed from an illuminating lamp 85 that illuminates the surface of the cornea HC of the eyeball EY that constitutes the object of treatment, an objective lens 81 that receives the light that passes through the dichroic mirror 62 from the cornea HC illuminated by the illuminating lamp 85, a prism 82 that reflects the light from the objective lens 81, and an ocular lens 83 that receives this light. This observation optical device 80 is devised so that an enlarged image of the cornea HC can be observed via the ocular lens 83.

Furthermore, in this example, control of the movement of the X-Y moving table 3 is accomplished by manual control. However, it would also be possible to install a shape measuring device that measures the shape of the cornea HC, and to install a device that automatically controls the operation of the X-Y moving table 3 on the basis of the shape of the corneal surface measured by the shape measuring device so that irradiation with laser light is performed automatically, i.e., an irradiation position regulating device.

Figure 11:
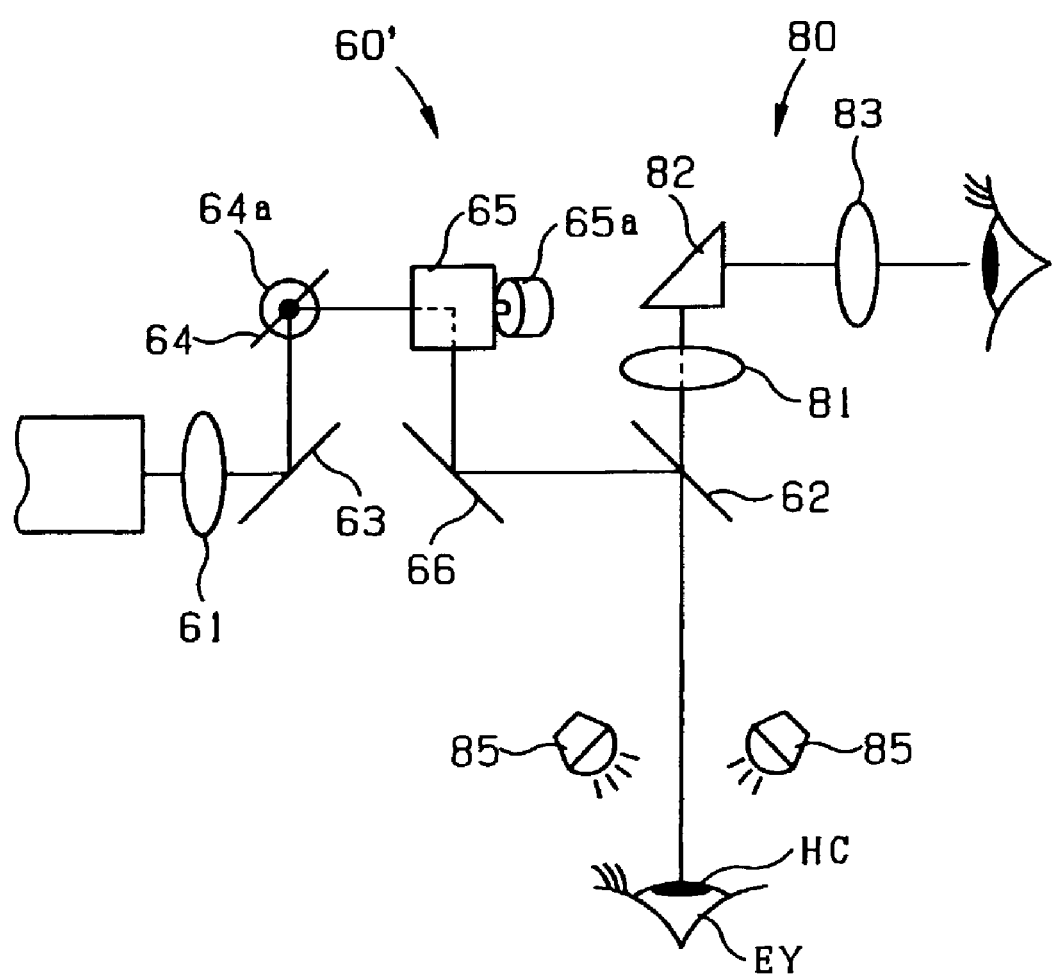
FIG. 11 is an explanatory diagram which shows the construction of a second working configuration of the irradiation optical device and observation optical device that form parts of the above-mentioned laser treatment apparatus.

In the example described above, the system is arranged so that the laser light spot that irradiates the surface of the cornea HC is manipulated by using the X-Y moving table 3 to move the apparatus as a whole in the horizontal plane. However, optical scanning of the laser light irradiation position would also be possible. Such an example is shown in FIG. 11. Here, the irradiation optical device 60' has a focusing lens 61 that focuses the laser light with a wavelength of 193 nm that is emitted from the above-mentioned laser apparatus 10 into the form of a slender beam, and is constructed so that the beam-form laser light thus focused is reflected by a first reflective mirror 63 and caused to be incident on a first servo mirror 64, the laser light is then reflected by the first servo mirror 64 and caused to be incident on a second servo mirror 65, the laser light reflected from the second servo mirror 65 is reflected by a second reflective mirror 66 and caused to be incident on the dichroic mirror 62, and the laser light reflected from the dichroic mirror 62 is caused to irradiate the surface of the cornea HC of the eyeball EY that constitutes the object of treatment. Furthermore, in the apparatus shown in FIG. 11, parts that are the same as in the apparatus shown in FIG. 10 are labeled with the same numbers, and redundant descriptions are omitted.

The first and second servo mirrors 64 and 65 have servo motors 64a and 65a that regulated the respective angles of the mirror surfaces. Ablation of the surface of the cornea is performed by using the servo motors 64a and 65a to move the angles of the mirror surfaces so that the laser light spot that irradiates the surface of the cornea HC is caused to perform a scanning movement; in this way, myopia, hyperopia or astigmatism, etc., is treated. Furthermore, in this case as well, the person performing the operation, such as an ophthalmologist, controls the operation of the servo motors 64a and 65a while visually observing the surface of the cornea HC via the observation optical device 80. Furthermore, it would also be possible to install a shape measuring device that measures the shape of the cornea HC, and to install a device that automatically controls the operation of the servo motors 64a and 65a so that irradiation with the laser light is automatically performed on the basis of the shape of the corneal surface measured by the shape measuring device, i.e., to install an irradiation position regulating device, in the same manner as described above.

Thus, myopia, hyperopia or astigmatism, etc., is treated by irradiating the surface of the cornea with pulsed laser light generated by the laser apparatus 10, so that the surface of the cornea is ablated. In this case, since the laser light generated by the laser apparatus 10 is pulse-form laser light with an extremely high frequency of 100 kHz (pulse width: 1 ns), smooth scanning is possible even if the pulsed light spot is scanned across the surface of the cornea. Furthermore, since the pulse width is extremely small, almost all of the pulse energy is used in the scission of material bonds, so that the occurrence of thermal volatilization is suppressed. Furthermore, in the laser treatment apparatus of the present invention, the pulse width and repetition frequency of the pulsed light (pulse-form laser light) can be controlled, so that a pulse width (specifically, a pulse width of 0.5 ns to 3 ns) and repetition frequency (specifically, a repetition frequency of 10 kHz to 100 kHz) that make it possible to suppress the occurrence of thermal volatilization in a favorable manner can be realized.

Figure 12:
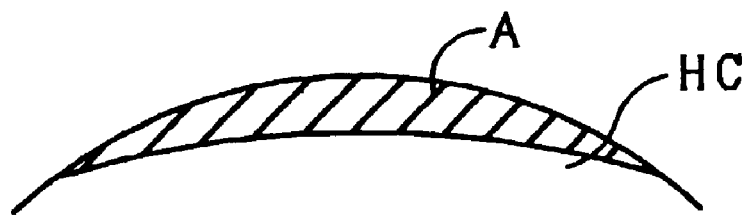
FIG. 12 is an explanatory diagram which shows the surface shape of the cornea constituting the object that is treated by the laser treatment apparatus of the present invention.

The treatment of myopia using such a laser treatment apparatus is accomplished (for example) by irradiating the hatched portion A of the surface of the cornea HC shown in FIG. 12 with laser light from the laser apparatus 10 so that this portion is volatilized and ablated. In the case of the laser treatment apparatus shown in FIGS. 10 and 11, ablation of the hatched portion A is accomplished by causing a scanning movement of the laser light spot that irradiates the surface of the cornea. However, ablation may also be accomplished using a laser treatment apparatus of the type shown in FIG. 13. Furthermore, in the laser treatment apparatus shown in FIG. 13, parts that are the same as those of the apparatus shown in FIGS. 10 and 11 are labeled with the same numbers, and this apparatus will be described.

Figure 13:
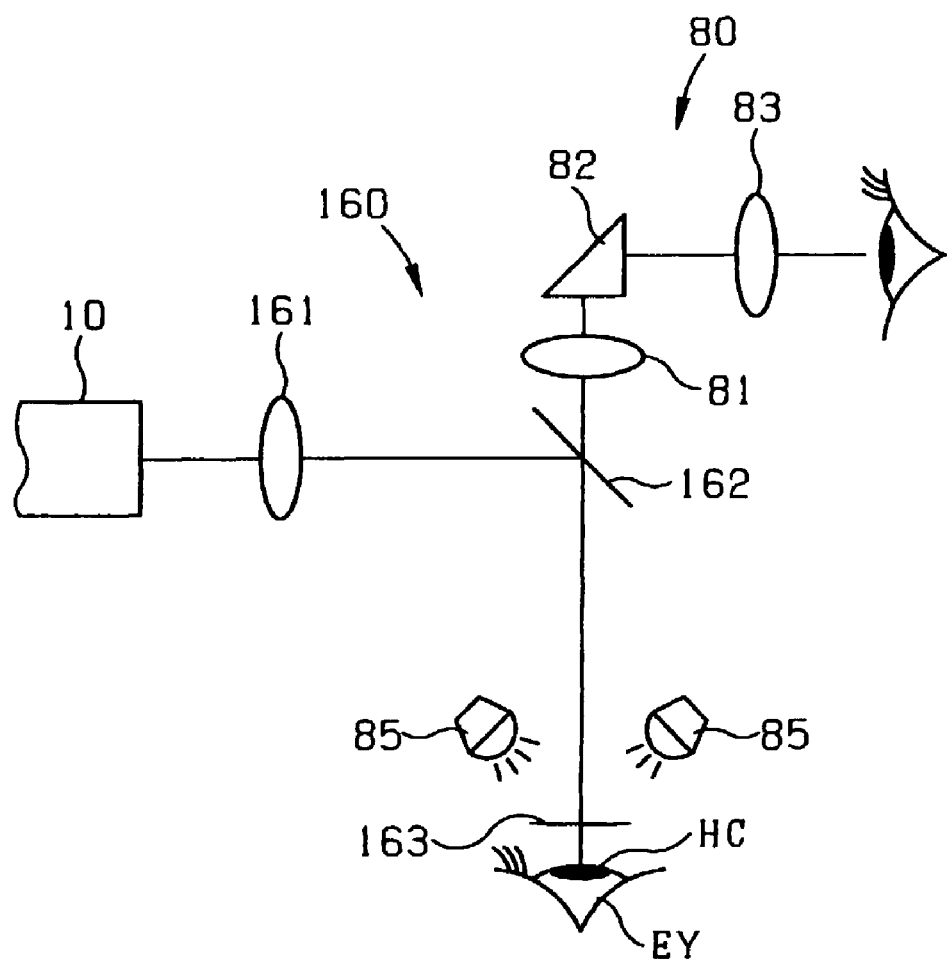
FIG. 13 is an explanatory diagram which shows the construction of a third working configuration of the irradiation optical device and observation optical device that form parts of the above-mentioned laser treatment apparatus.

The apparatus shown in FIG. 13 is constructed from an irradiation optical device 160 and an observation optical device 80. The observation optical device 80 has the same construction as that described above; accordingly, a description of this observation optical device is omitted. The irradiation optical device 160 is constructed from a focusing lens 161 that focuses the laser light with a wavelength of 193 nm that is emitted from the laser apparatus 10 into the form of a cylindrical beam with a specified size, a dichroic mirror 162 that reflects the focused cylindrical beam-form laser light and causes this laser light to irradiate the surface of the cornea HC of the eyeball EY that constitutes the object of treatment, and a filter 163 that is disposed in a position near the eyeball EY.

Figure 14:
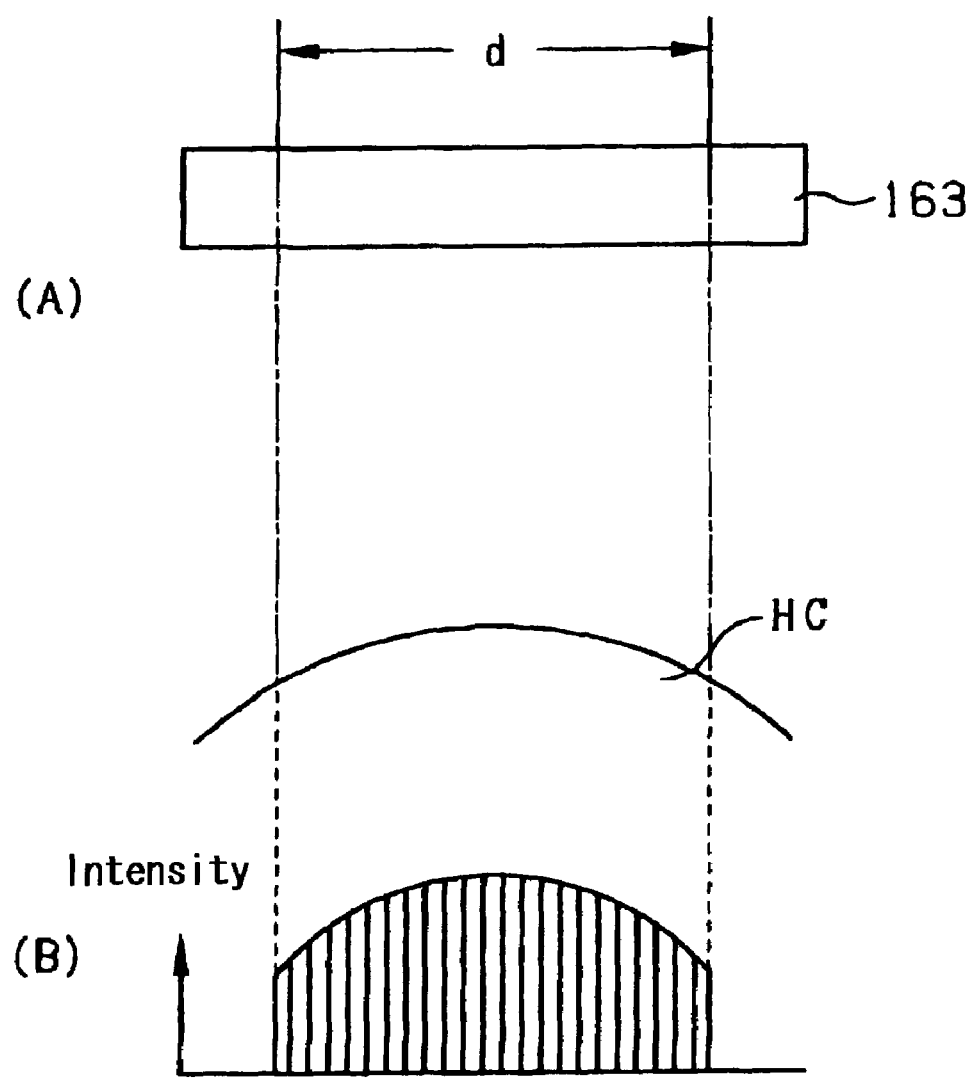
FIG. 14 is an explanatory diagram which shows the peripheral structure of the filter that forms a part of the irradiation optical device in the above-mentioned third working configuration, as well as the filter performance.

As is shown in FIG. 14, the cylindrical beam-form laser light that is created by the focusing lens 161 consists of cylindrical laser light with a diameter d that is sufficient to cover the region constituting the object of treatment on the surface of the cornea HC. The filter 163 has a performance which shows good transmission of the laser light in the central portion, and which shows a decrease in transmissivity in the peripheral portions of the filter. When the cylindrical beam-form laser light passes through the filter 163, the intensity of this laser light has a distribution such as that shown in FIG. 14(b). When the surface of the cornea HC is irradiated with laser light that has such an intensity distribution, the amount of ablation is large in the area where the intensity is large, so that ablation that removes the hatched portion A shown in FIG. 12 is accomplished. This corresponds to the irradiation control device stipulated in the claims; this irradiation control device regulates the irradiation intensity of the laser light with respect to the treatment site.

Furthermore, a plurality of light blocking members that have openings of a specified shape may also be used instead of the filter 163. For example, it would also be possible to arrange a plurality of light blocking members with different diameters on a concentric circle, and to cause ablation of the hatched portion A shown in FIG. 12 by first ablating the central portion of the cornea HC using a light blocking member with a small opening, and then repeating ablation while replacing the light blocking member so that the opening area gradually increases. This corresponds to the irradiation control device stipulated in the claims; this irradiation control device regulates the irradiation region of the laser light with respect to the treatment site.

In the above-mentioned laser treatment apparatus, the intensity of the laser light that irradiates the surface of the cornea HC is closely related to the magnitude of the ablation that is performed; accordingly, it is necessary to regulate the intensity of the laser light. This intensity regulation can easily be accomplished by regulating the oscillation frequency of the laser 12 inside the laser apparatus 10, or controlling the amount of light generated by the semiconductor lasers 31a and 31b in the third-stage fiber light amplifiers 30. This corresponds to the intensity regulating device that regulates the intensity of the laser light as stipulated in the claims. Furthermore, for the purpose of such intensity regulation, it would also be possible to install a laser light intensity measuring device that measures the actual laser light intensity, to judge whether or not the actual laser light intensity measured by this laser light intensity measuring device is the desired intensity, and to determine that this intensity must be corrected in cases where the intensity deviates from the desired intensity. This intensity correction can be accomplished by controlling the operation of the above-mentioned intensity regulating device; the laser light intensity correction device stipulated in the claims can be used for such control of the operation of the intensity regulating device.

In the above examples, a DFB semiconductor laser 12 and fiber amplifiers were used as the laser light source in the laser light generating part 11; however, instead of this, it would also be possible to use a Q-switched pulsed Er:YAG laser or a Q-switched pulsed Er:glass laser. In such cases, laser light with a wavelength of approximately 1550 nm is output, and laser light with a wavelength of 194 nm, which constitutes the octuple harmonic, can be obtained by subjecting this laser light to wavelength conversion.

INDUSTRIAL APPLICABILITY

As was described above, the laser treatment apparatus of the present invention can be used to treat myopia or astigmatism, etc., by correcting the curvature or indentations and projections in the cornea through the ablation of the surface of the cornea (PRK: photorefractive keratectomy) or ablation of the interior of the cornea in which an incision has been made (LASIK: laser intrastromal keratomileusis) by irradiation of the cornea with laser light. Of course, the field of utilization of the present invention is not limited only to the above-mentioned treatment of the cornea; the present invention may also be utilized in other treatments.

The invention claimed is:
1. A laser treatment apparatus comprising:
    a laser apparatus, including:
    a laser light generating device having a solid-state laser that generates laser light of a specified wavelength,
    a light amplifier that amplifies the laser light generated by the laser light generating device,
    a wavelength converter which uses a nonlinear optical crystal to convert the laser light amplified by the light amplifier into treatment laser light with a wavelength of approximately 193 nm, and
    an irradiation optical device which delivers the treatment laser light generated by the laser apparatus to a treatment site, and irradiates the treatment site with the treatment laser light,
    wherein the solid-state laser comprises a DFB semiconductor laser or fiber laser that has an oscillation wavelength in the range of 1.51 $\mu$m to 1.59 $\mu$m, and the wavelength converter converts the laser light from the solid-state laser into an octuple harmonic that is in the range of 189 nm to 199 nm.

* * * * *